United States Patent [19]

Myers

[11] 4,225,419
[45] Sep. 30, 1980

[54] ALUMINA ISOMERIZATION PROCESS

[75] Inventor: John W. Myers, Bartlesville, Okla.

[73] Assignee: Phillips Petroleum Company, Bartlesville, Okla.

[21] Appl. No.: 30,982

[22] Filed: Apr. 18, 1979

[51] Int. Cl.$^3$ .................... C10G 35/06; C10G 63/04; C07C 5/27; B01J 21/20
[52] U.S. Cl. .................................. 208/135; 208/70; 585/671; 252/416; 252/419; 252/420
[58] Field of Search ...................... 252/416, 419, 420; 585/671, 664; 208/70, 135

[56] References Cited

U.S. PATENT DOCUMENTS

| | | | |
|---|---|---|---|
| 2,422,884 | 6/1947 | Burgin | 585/671 |
| 2,546,031 | 3/1951 | Hanson | 252/416 |
| 3,546,132 | 12/1970 | Godin | 252/419 |
| 3,558,733 | 6/1971 | Myers | 585/671 |
| 3,631,219 | 12/1971 | Myers | 585/671 |

Primary Examiner—P. E. Konopka

[57] ABSTRACT

A process for isomerizing olefins to more highly branched olefins with certain alumina isomerization catalysts wherein coke formation is reduced by regenerating the catalysts with a wet regenerating gas.

20 Claims, No Drawings

ALUMINA ISOMERIZATION PROCESS

This invention relates to the isomerization of hydrocarbons with an alumina isomerization catalyst. In another aspect this invention relates to the regeneration of an alumina isomerization catalyst.

It is known that alumina catalysts can be effective in the isomerization of hydrocarbons, particularly in the conversion of olefins to corresponding more highly branched olefins. During such isomerization reactions coke forms upon the alumina and eventually the catalyst begins to become inactive. In addition to fouling the catalyst, coke formation is undesirable in that it is the result of the conversion of feedstock olefin into an undesired product, i.e. carbon. Accordingly, there is a need for methods for reducing coke buildup on alumina isomerization catalyst.

An object of the present invention is to provide a method of reducing coke formation during isomerization reactions employing alumina catalysts.

Still another object of the present invention is to provide a novel method of isomerizing olefins.

Other objects, aspects, and advantages of the present invention will be apparent from the following disclosure.

In accordance with the present invention the amount of coke formed during an isomerization of an olefin with certain alumina isomerization catalysts is reduced by regenerating the alumina in presence of a free oxygen-containing gas which further contains about 0.3 to about 10 mole percent water based on the moles of free oxygen-containing gas. Preferably the free oxygen-containing gas contains about 0.5 to about 5 mole percent water.

The present invention is applicable to those alumina isomerization catalysts having a surface area of at least about 100 m$^2$/g, preferably the surface area is greater than 150 m$^2$/g. Techniques of preparing such alumina catalysts are well known in the art. Examples of such alumina catalysts include eta-alumina and gamma-alumina.

The best isomerization catalysts are those aluminas having high purity, particularly with respect to their content of alkali metals. Thus generally the aluminas should contain less than about 0.1 weight percent alkali metal, preferably less than 0.05 weight percent, based on the weight of the catalyst. The alkali metals include lithium, sodium, potassium, rubidium, and cesium.

Such catalysts can be employed in the manner known in the art for the skeletal isomerization of olefins to more highly branched olefins. Such catalysts are particularly suitable for the isomerization of n-olefins having 4 to 10 carbon atoms per molecule or mixtures thereof. Mixtures comprising olefins and essentially inert hydrocarbons can also be treated according to this invention to provide an isomerized olefinic product in admixture with the inert hydrocarbons. Particularly useful isomerizations with such catalysts are conducted on feedstreams of gasoline, especially catalytically cracked gasoline.

The isomerization with such catalysts can be conducted under any conditions sufficient to produce the desired isomers. Generally the isomerization is conducted at a temperature in the range of about 315° C. to about 510° C., preferably about 343° C. to about 454° C. Isomerization is generally not affected significantly by pressure, but elevated pressures can accelerate some undesirable olefin reactions, such as polymerization. Hence low reaction pressure is generally favored. Partial pressure of the hydrocarbon during the isomerization generally will be in the range of about atmospheric to about 200 psig (i.e. about $1.03 \times 10^5$ to about $1.48 \times 10^6$ Pa), more preferably the reaction pressure for isomerization does not exceed 100 psig ($7.9 \times 10^5$ Pa). Typically the contact time for the hydrocarbon in such isomerization reactions, expressed in volumes of liquid feedstock per volume of catalyst per hour (LHSV), is in the range of about 0.1 to about 15, preferably about 0.5 to about 5.

When the activity of the catalyst has declined below a desired level the flow of hydrocarbon to the catalyst is stopped and the catalyst is regenerated in accordance with the instant invention.

Generally the regeneration involves contacting the deactivated catalyst with the "wet" free oxygen-containing gas at a temperature in the range of about 425° C. to about 705° C., preferably at a temperature no greater than 650° C. Pressure is not critical to the process of oxidative regeneration but elevated pressure, e.g. pressures in the range of about 50 to about 200 psig (about $4.5 \times 10^5$ to about $1.48 \times 10^6$ Pa) may be desirable for economic reasons.

The free oxygen-containing gas can include air or, preferably, air which has been further diluted with an inert gas such as nitrogen. Water can be added to the free oxygen-containing gas in any suitable manner. For example steam can be added to the free oxygen-containing gas.

In switching from isomerization to regeneration it is usually desirable to purge the catalyst of hydrocarbon before introducing the free oxygen-containing gas. Similarly, in making the transition from regeneration to olefin isomerization, it is usually desirable to purge the catalyst of free oxygen-containing gas before the catalyst is contacted with the hydrocarbon feedstream. Such purging can be accomplished by use of a suitably inert gas such as, for example, nitrogen. Preferably this purging gas will also contain water vapor.

The present invention will be further illustrated by reference to the following example.

EXAMPLE

The effect of using wet and dry regeneration gases on three alumina isomerization catalysts was evaluated. Pertinent properties of the three catalysts are set forth in Table I.

Table I

| Alumina | Surface Area, m$^2$/g | Na Content, Wt. %* |
|---|---|---|
| A | 249 | 0.015 |
| B | 219 | 0.003 |
| C | 85 | 0.1 |

*Typical concentration, supplied by manufacturer.

Each of the three catalysts was employed in a series of isomerization runs using as a feed in all runs a full range catalytically cracked gasoline that had an unleaded research octane number (RON) of 86.7. Each isomerization run with each catalyst run was at about 30 psia ($2.0 \times 10^5$ Pa) and of five hours duration. Each isomerization run was followed by a regeneration. The isomerizations were all conducted at a temperature in the range of about 370° C. to about 430° C. Regeneration with a free oxygen-containing gas was initiated at about 480° C; the temperature of the catalyst increased temporarily during the regeneration step because of the heat of combustion released during oxidation of the deposited coke. The wet regeneration gas contained about 2.5 to about 3.0 mole percent water vapor. The dry regeneration gas was essentially water free. Generally, after each run the RON of the product and/or the amount of coke on the catalyst was determined. The research octane number was determined using standard ASTM methods. Table II below sets forth some typical results of the effect of regenerating with wet or dry gas.

TABLE II

| Catalyst | Isomerization Temp., °C. | LHSV | Run No. | Regeneration Gas | Coke, Wt. % of Catalyst | Unleaded RON |
|---|---|---|---|---|---|---|
| A | 402 | 1.10 | 79 | Dry | 3.15 | 89.3 |
| A | 402 | 1.11 | 80 | Wet | 2.31 | 89.5 |
| B | 398 | 1.07 | 18 | Dry | 3.54 | * |
| B | 399 | 1.09 | 21 | Wet | 2.42 | 88.7 |
| C | 400 | 1.14 | 8 | Dry | 2.26 | 88.1** |
| C | 399 | 1.18 | 10 | Wet | 2.59 | 88.3** |

*Not determined.
**Determined on product of substantially identical runs made to provide enough material for the octane measurement.

All runs set forth in Table II where RON was evaluated showed an increase in the RON of the product, indicating that all those runs provided some isomerization. Catalysts A and B, which are high surface area catalysts within the scope of this invention, produced significantly less coke when having been regenerated with wet gas than with dry. In contrast, catalyst C, a low surface area catalyst outside the scope of this invention, showed the opposite result.

Reasonable variations and modifications are possible within the scope of this disclosure without departing from the scope and spirit thereof.

What is claimed is:

1. A process for regenerating an isomerization catalyst consisting essentially of alumina having a surface area of at least about 100 m$^2$/g and having coke deposited thereon comprising heating said catalyst at a temperature in the range of about 425° C. to about 705° C. in the presence of a free oxygen-containing gas containing about 0.3 to about 10 mole percent water based on the moles of free oxygen-containing gas for a time sufficient to burn off substantially all the coke on said catalyst.

2. A process according to claim 1 wherein said isomerization catalyst is selected from the group consisting of eta-alumina and gamma-alumina.

3. A process according to claim 2 wherein the temperature of regeneration is no greater than about 650° C.

4. A process according to claim 3 wherein said catalyst contains less than 0.1 weight percent alkali metal based on the weight of the catalyst and a surface area greater than 150 m$^2$/g.

5. In a process for the isomerization of an olefin-containing feedstream using an isomerization catalyst consisting essentially of alumina having a surface area of at least about 100 m$^2$/g wherein one isomerization run is followed by catalyst regeneration and then an additional isomerization run, the improvement which comprises carrying out said regeneration by heating said catalyst at a temperature in the range of about 425° C. to about 705° C. in the presence of a free oxygen-containing gas containing about 0.3 to about 10 mole percent water based on the moles of free oxygen-containing gas for a time sufficient to burn off substantially all the coke on said catalyst.

6. A process in accordance with claim 5 wherein said isomerization catalyst is selected from the group consisting of eta-alumina and gamma-alumina.

7. A process in accordance with claim 6 wherein the temperature of regeneration is no greater than about 650° C.

8. A process in accordance with claim 7 wherein the said olefin-containing feedstream contains one or more n-olefins having four to 10 carbon atoms per molecule.

9. A process in accordance with claim 8 wherein the isomerizations are conducted upon a feedstream of gasoline.

10. A process in accordance with claim 9 wherein the gasoline comprises at least one catalytically cracked gasoline fraction.

11. A process in accordance with claim 10 wherein said catalyst contains less than 0.1 weight percent alkali metal based on the weight of the catalyst and has a surface area greater than 150 m$^2$/g.

12. A cyclic process for the isomerization of at least one olefin having from 4 to 10 carbon atoms per molecule comprising:
(a) contacting an active isomerization catalyst consisting essentially of alumina having a surface area of at least about 100 m$^2$/g with a feedstream containing one or more olefins having from 4 to 10 carbon atoms per molecule under conditions suitable for isomerizing said one or more olefins to more highly branched olefins,
(b) regenerating the catalyst employed in step (a) by heating said catalyst at a temperature in the range of about 425° C. to about 705° C. in the presence of a free oxygen-containing gas containing about 0.3 to about 10 mole percent water based on the moles of free oxygen-containing gas for a time sufficient to burn off substantially all the coke on said catalyst, and thereafter
(c) contacting the regenerated catalyst from step (b) with a feedstream containing one or more olefins having 4 to 10 carbon atoms per molecule under conditions suitable for isomerizing said one or more olefins to more highly branched olefins.

13. A process in accordance with claim 12 wherein said alumina isomerization catalyst is selected from the group consisting of eta-alumina and gamma-alumina.

14. A process in accordance with claim 13 wherein the temperature of regeneration is no greater than about 650° C.

15. A process in accordance with claim 14 wherein said feedstream contains one or more n-olefins having four to 10 carbon atoms per molecule.

16. A process in accordance with claim 15 wherein the isomerizations are conducted upon a feedstream of gasoline.

17. A process in accordance with claim 16 wherein the gasoline comprises at least one fraction of catalytically cracked gasoline.

18. A process in accordance with claim 16 wherein the free oxygen-containing gas employed in the regeneration contains about 2.5 to about 3.0 mole percent water based on the moles of the free oxygen-containing gas.

19. A process according to claim 4 wherein said free-oxygen-containing gas contains about 2.5 to about 3.0 mole percent water based on the moles of the free oxygen-containing gas.

20. A process according to claim 11 wherein said free-oxygen-containing gas contains about 2.5 to about 3.0 mole percent water based on the moles of the free oxygen-containing gas.

* * * * *